United States Patent [19]

Ichikawa et al.

[11] 4,116,955
[45] Sep. 26, 1978

[54] INCLUSION COMPLEX COMPOUND, PROCESS FOR ITS PRODUCTION, AND METHOD FOR ITS USE

[75] Inventors: Yataro Ichikawa; Mamoru Yamamoto; Hideki Tsuruta; Kenichi Kato, all of Iwakuni; Teizo Yamaji, Hachioji; Eishin Yoshisato; Toshiyuki Hiramatsu, both of Hino, all of Japan

[73] Assignee: Teijin Limited, Osaka, Japan

[21] Appl. No.: 802,022

[22] Filed: May 31, 1977

[30] Foreign Application Priority Data

Jun. 18, 1976 [JP] Japan .................. 51/66044

[51] Int. Cl.² .................. C07C 107/00; C09B 27/00; C11C 1/00; C09F 5/00
[52] U.S. Cl. .................. 260/192; 260/404; 260/413; 260/410.9 R; 260/681.5 R; 260/677 A; 260/652 P; 260/593 P; 260/601 R; 260/455 R; 260/583 R; 260/583 N; 260/502.6; 260/513 R; 260/454; 260/456 R; 260/616; 560/248; 560/249; 560/261
[58] Field of Search ........ 260/192, 404, 413, 410.9 R, 260/681.5 R, 677 A, 652 P, 593 P, 601 R, 631.5, 643 D, 643 F, 643 G, 455 R, 616, 454, 456 R, 502.6, 513 R; 560/248, 249, 261

[56] References Cited

U.S. PATENT DOCUMENTS 4,028,385 7/1977 Fujita et al. .................. 260/410.9 R

OTHER PUBLICATIONS

Zapata et al., Chemical Abstracts, vol. 54:17804e.
Tomus; R., Chemical Abstracts, vol. 81:89903q (1974).

*Primary Examiner*—Patrick Garvin
*Assistant Examiner*—John F. Niebling
*Attorney, Agent, or Firm*—Sherman & Shalloway

[57] ABSTRACT

An inclusion complex compound comprising (a) meta-cyclophane and (b) a trans-terpenoid of the formula

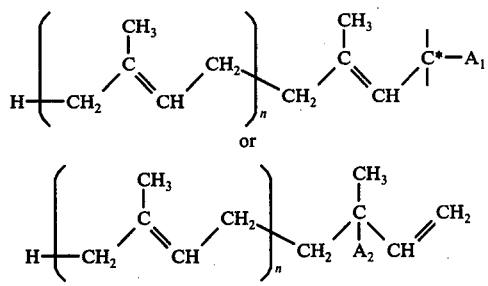

wherein n is an integer of 1 to 9; $A_1$ and $A_2$ each represent (1) a hydrogen atom, (2) a halogen atom, (3) an inorganic group containing an oxygen, nitrogen or sulfur atom, (4) an organic group containing 1 to 5 carbon atoms, or (5) an organic group containing an oxygen, nitrogen or sulfur atom and 1 to 5 carbon atoms; and C* is the carbon atom of a carbonyl or methylene group, included by the meta-cyclophane. This inclusion complex compound can be prepared by contacting the meta-cyclophane with a mixture containing the trans-terpenoid. A trans-terpenoid can be separated from a mixture containing it by utilizing an inclusion complex compound of it with meta-cyclophane.

11 Claims, No Drawings

INCLUSION COMPLEX COMPOUND, PROCESS FOR ITS PRODUCTION, AND METHOD FOR ITS USE

This invention relates to an inclusion complex compound comprising meta-cyclophane as a host and a certain trans-terpenoid as a guest, a process for its production, and to a process for separating isomers by using it.

Little has been known about a host compound which can selectively include only an all-trans-terpenoid as a guest compound from a stereoisomeric terpenoid mixture, and a technique of separating isomers utilizing such an inclusion complex compound. The prior art only developed a process for separating solanesol (guest) from a solanesol mixture extracted from a naturally occurring material which comprises including it in thiourea (host) (Japanese Patent Publication No. 28800/72), and a process for separating a trans-isomer (guest) at the side chain of vitamin A by including it in tetrachlorohydroquinone (host) (Japanese Patent Publication No. 22976/68). These processes, however, have the defect that the separation of the desired isomer (guest) from the resulting inclusion complex compound involves complicated steps.

It is an object of this invention therefore to provide a process for separating an all-trans-terpenoid with good efficiency by utilizing a specific host compound, which can selectively include only the all-trans-terpenoid as a guest from a stereoisomeric terpenoid mixture to form an inclusion complex compound and permit the releasing of the guest from the inclusion complex compound by a simple operation.

We have found that meta-cyclophane (host) of the following formula

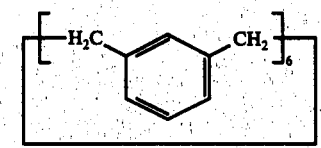
(I)

exhibits a marked inclusion selectivity for a trans-terpenoid (guest) of the following formula (in which all isoprene skeletons are bonded in a trans form)

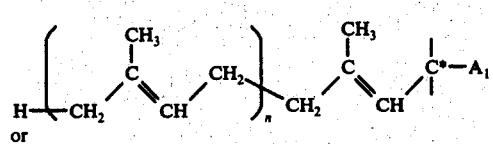
(II-1)

or

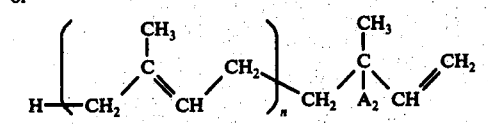
(II-2)

wherein $n$ is an integer of 1 to 9; $A_1$ and $A_2$ each represent (1) a hydrogen atom, (2) a halogen atom, (3) an inorganic group containing an oxygen, nitrogen or sulfur atom, (4) an organic group containing 1 to 5 carbon atoms, or (5) an organic group containing an oxygen, nitrogen or sulfur atom and 1 to 5 carbon atoms; and C* represents the carbon atom of a carbonyl or methylene group.

Thus, the present invention provides (1) an inclusion complex compound comprising meta-cyclophane of formula (I) and at least one trans-terpenoid of formula (II-1) or (II-2) included therein;

(2) a process for producing the inclusion complex compound of (1) above, which comprises contacting meta-cyclophane of formula (I) with an isomeric mixture containing at least one trans-terpenoid of formula (II-1) or (II-2); and (3) a process for separating trans-terpenoid, which comprises contacting meta-cyclophane of formula (I) with an isomeric mixture containing at least one trans-terpenoid of formula (II-1) or (II-2) to form an inclusion complex compound comprising meta-cyclophane and trans-terpenoid included therein, separating the inclusion complex compound from the mixture, and then separating the included trans-terpenoid from the inclusion complex compound.

The meta-cyclophane of formula (I) is a known compound which can be prepared by known methods, for example those described in Helvetica Chimica Acta. Vol. 50, F₂sciculus 7 (1967), No. 204, and Synthesis, 424 (1974).

The trans-terpenoid of formula (II-1) or (II-2) is characterized in that all the isoprene skeletons, namely the structure of the formula

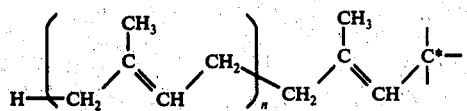

in formula (II-1) and the structure of the formula

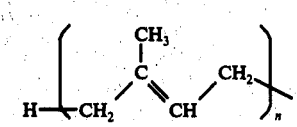

in formula (II-2) consist of trans bonds.

Of the trans-terpenoids of formulae (II-1) and (II-2), preferred species for the practice of the present invention are those in which $n$ is an integer of 1 to 5, and $A_1$ and $A_2$ each represent (1) a hydrogen atom, (2) a halogen atom selected from chlorine, bromine and iodine, (3) an inorganic group selected from —OH, —NH₂, —NO₂, —SH, —SCH and —SO₃H, (4) an alkyl group containing 1 to 5 carbon atoms such as —CH₃, —C₂H₅ or —C₃H₇, or (5) a group selected from —OR,

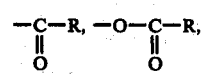

—NHR, —N=N—R, —SO₂R, and —SR, in which R is an alkyl group containing 1 to 5 carbon atoms.

More preferred species of the preferred trans-terpenoids of formulae (II-1) and (II-2) are those in which $A_1$ and $A_2$ each represent —H, —Cl, —Br, —OH, —NH₂, —NO₂, —SH, —SO₃H, —CH₃, —OR,

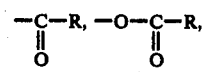

—NHR, or —SR. These atoms or groups may be bonded to a carbon atom through an alkylene group. In this case, the sum of the number of the carbon atoms of the alkylene group and that of the carbon atoms of group R should not exceed 5.

Especially preferred trans-terpenoids in the practice of this invention are those of the above formulae in which $A_1$ and $A_2$ each represent —H, —Cl, —Br, —OH, —NH$_2$, —OCH$_3$, —OC$_2$H$_5$, —OC$_3$H$_7$, —CH$_4$—H$_9$,

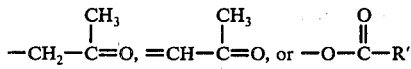

in which R' is an alkyl group containing 1 to 3 carbon atoms.

The trans-terpenoids of the above formulae have great utility in various industrial fields, and those in which n is 1 to 4 are widely used. For example, trans-terpenoids with n being 1 or 2 are important compounds as perfumes, perfume intermediates and pharmaceutical intermediates; trans-terpenoids with n being 3, as vitamins K$_2$ and tocotrienols; and long-chained trans-terpenoids with n being 5 to 9, as a side-chain forming material for coenzymes Q.

Examples of the compounds of formula (II-1) are 3,7-dimethyl-2,6-octadiene, 6,10-dimethyl-5,9-undecadien-2-one, 6,10-dimethyl-3,5,9-indecatrien-2-one, 3,7-dimethyl-2,6-octadiene-1 al (citral) 3,7-dimethyl-2,6-octadien-1-ol (geraniol), geranyl methyl ether, geranyl bromide, geranyl chloride, 3,7-dimethyl-2,6-octadiene-1-carboxylic acid (geranic acid), methyl geranate, ethyl geranate, geranic acid amide, geranyl formate, geranyl acetate, geranyl propionate, 2,6-dimethyl-1,5-hexadien-1-ol, 2,6-dimethyl-1,5-hexadiene-methyl ether geranylacetic acid, 3,7,11-trimethyl-2,6-10-dodecatriene, 6,10,14-trimethyl-5,9,13-pentadecatrien-2-one (farnesyl acetone), 6,10,14-trimethyl-3,5,9,13-pentadecatetraen-2-one, 3,7,11-trimethyl-2,6,10-dodecatrien-1-al (farnesal), 3,7,11-trimethyl-2,6,10-dodecatrien-1-ol (farnesol), farnesyl methyl ether, farnesyl bromide, farnesyl chloride, 3,7,11-trimethyl-2,6,10-dodecatriene-1-carboxylic acid (farnesic acid), methyl farnesate, ethyl farnesate, farnesic acid amide, farnesyl acetate, farnesyl formate, farnesyl propionate, 2,6,10-trimethyl-1,5-9-undecatrien-1-ol, 2,6,10-trimethyl-1,5,9-undecatriene methyl ether, farnesylacetic acid, 3,7,11,15-tetramethyl-2,6,10,14-hexadecatetrane, 6,10,14,19-tetramethyl-5,9,13,17-nonadecatetraen-2-one (geranyl geranyl acetone), 6,10,14,19-tetramethyl-3,5,9,13,17-nonadecapentaen-2-one, 3,7,11,15-tetramethyl-2,6,10,14-hexadecatetraen-1-al (geranyl geranial), 3,7,11,15-tetramethyl-2,6,10,14-hexadecatetraen-1-ol (geranyl geraniol), geranyl geranyl methyl ether, geranyl geranyl bromide, geranyl geranyl chloride, 3,7,11,15-tetramethyl-2,6,10,14-hexadecatetraen-1-carboxylic acid (geranyl geranic acid), methyl geranylgeranate, ethyl geranylgeranate, geranylgeranic acid amide, geranyl geranylacetate, geranyl geranylformate, geranyl geranyl propionate, 2,6,10,14-tetramethyl-1,5,9,13-pentadeca-1-ol, 2,6,10,14-tetramethyl-1,5,9,13-pentadeca-methyl ether, geranylgeranylacetic acid, geranyl farnesyl acetic acid, 4-farnesyl farnesyl-3-methyl-2-butene, geranyl-farnesyl acetone, farnesylfarnesyl geranyl acetone, dehydro-solanesyl acetone, farnesylfarnesal, farnesyl farnesyl citral, solanesyl citral, geranyl farnesol, solanesol, farnesyl farnesyl geranyl geraniol, farnesyl farnesylcarboxylic acid, methyl farnesylfarnesylcarboxylate, solanesyl acetate, 3-geranylgeranyl-2-methyl-1-propan-1-ol, and solanesylacetic acid.

Examples of the compounds of formula (II-2) include 3,7-dimethyl-1,6-octadien-3-ol (linalol), 3,7-dimethyl-3-methoxy-1,6-oxtadiene, 3,7-dimethyl-1,6-octadiene (3-dihydro-myrcene), 3,7,11-trimethyl-1,6,10-dodecatrien-3-ol (nerolidol), 3,7,11-trimethyl-3-methoxy-1,6,10-dedecatriene, 3,7,11-trimethyl-1,6,10-dodecatriene (farnesene), 3,7,11,15-tetramethyl-1,6,10,14-hexadecatetraen-3-ol, 3,11,15-tetramethyl-3-methoxy-1,6,10,14-hexadecatetraene, 3,7,11,15-tetramethyl-1,6,10,14-hexadecatetraene (geranyl geranylene), and 4-solanesyl-3-methyl-1-buten-3-ol.

Various methods can be used to prepare the inclusion complex compound of meta-cyclophane of formula (I) and the trans-terpenoid of formula (II-1) or (II-2). For example, this can be achieved by merely adding meta-cyclophane to a mixture containing the trans-terpenoid. In order to perform the including reaction completely, the resulting mixture may be heated.

The amount of the meta-cyclophane of formula (I) used is 0.01 to 100 moles, preferably 0.01 to 50 moles, especially advantageously 0.05 to 20 moles, per mole of the trans-terpenoid of formula (II-1) or (II-2) in the mixture containing the trans-terpenoid.

The reaction of including the trans-terpenoid of formula (II-1) or (II-2) in the meta-cyclophane of formula (I) is carried out generally at −50° C. to 350° C., preferably 0° C. to 200° C., especially 20° C. to 150° C.

When the resulting inclusion complex compound precipitates from the mixture, it can be favorably separated by usual solid-liquid separating methods, for example filtration, centrifugal separation, or sedimentation. Or the separation can also be favorably achieved by evaporating the solvent and the non-included components from the mixture. On the other hand, when the resulting inclusion complex compound dissolves in the mixture without precipitation, it can be separated, for example, by a method comprising passing the mixture through a permselective membrane or molecular sieve, or by a method which comprises precipitating the inclusion complex compound by either cooling the mixture, evaporating a part of the solvent from the mixture or adding to the mixture a solvent which does not dissolve the inclusion complex compound or only slightly dissolve it, and then separating the resulting precipitate by the first-mentioned method. In any case, the separating operation is performed at a temperature of −50° C. to 150° C., preferably 0° C. to 90° C.

In the separation of the trans-terpenoid of formula (II-1) or (II-2) from the trans-terpenoid-containing mixture by including it in meta-cyclophane, there is no restriction in the content of the trans-terpenoid of formula (II-1) or (II-2) in the mixture. Even when its content is very low, the inclusion complex compound of this invention can be formed without any trouble. Needless to say, the inclusion of substances which impede the including reaction, substances which readily adsorb the trans-terpenoid of formula (II-1) or (II-2) from the resulting inclusion complex compound, and substances which readily dissolve the resulting inclusion complex compound in the mixture in addition to the trans-terpenoid (II-1) or (II-2) is not preferred.

The inclusion complex compound of this invention shows characteristic absorptions of both meta-cyclophane of formula (I) and the trans-terpenoid of formula (II-1) or (II-2) in infrared absorption spectroscopy. When the inclusion complex compound of this invention is subjected to differential thermal analysis, an abrupt weight loss which means the liberation of a trans-terpenoid occurs at a certain temperature. The inclusion complex compound of this invention also shows a certain inclusion ratio (to be described hereinbelow) for a given trans-terpenoid. These facts show that the inclusion complex compound of this invention is neither an ordinary compound of meta-cyclophane and a trans-terpenoid nor an ordinary mixture of meta-cyclophane and a trans-terpenoid.

The inclusion complex compound of this invention can be easily separated into the trans-terpenoid of formula (II-1) or (II-2) and the meta-cyclophane of formula (I) by various methods. This can afford pure trans-terpenoids of formula (II-1) or (II-2).

Various methods are used to separate the trans-terpenoid of formula (II-1) or (II-2) from the inclusion complex compound of this invention. Among those which can be advantageously used are (a) a method which comprises heating the inclusion complex compound to a temperature of 90° to 350° C., preferably 120° to 280° C., in the absence or presence of a medium to evaporate the trans-terpenoid, and (b) a method which comprises contacting the inclusion complex compound with a solvent such as n-hexane, benzene, cyclohexane, acetone, a p-alkyl-substituted benzene or tetrahydrofuran to separate the trans-terpenoid.

Generally, the number of cis-trans stereoisomers of terpenoid increases with an increase in the number represented by $n$ in formula (II-1) or (II-2). These isomers are close to one another in boiling point and other physical and chemical properties, and it is extremely difficult to separate these isomers on a commercial scale by using distillation or crystallization techniques, for example. Moreover, long-chained terpenoids are difficult to distill. Various attempts have therefore been made to synthesize trans-isomers by stereospecific reactions which yield trans-isomers as main products [JACS 89, 4245 (1967)], but none of them have yet gained commercial acceptance. Even on a laboratory scale, it is not easy to synthesize compounds of formula (II-1) or (II-2) in which $n$ is 2 or less. In the prior art, synthesis of trans-terpenoids with $n$ being at least 3 requires enormous time and costs and high levels of experimental techniques. In contrast, the present invention makes it possible to separate only a trans-terpenoid simply from a cis-trans mixed terpenoid synthesized by conventional methods. Thus, the present invention provides a process for producing trans-terpenoids which can be performed commercially. In this case, the yield of the trans-terpenoid increases if after the separation of the trans-isomer, the remaining cis-isomer is isomerized to a trans-isomer, and the resulting trans-isomer is then separated by the process of this invention. When the above isomerization reaction is carried out in the presence of meta-cyclophane, the trans-terpenoid formed by isomerization is successively included by the meta-cyclophane, and the resulting inclusion complex compound successively precipitates. Hence, this is a convenient procedure.

The following Examples illustrate the present invention in more detail.

In these Examples, MC stands for meta-cyclophane of formula (I).

The selectivity, $\beta(A/B)$, is a value calculated by the following equation.

$$\beta\left(\frac{A}{B}\right) = \frac{\left(\frac{C_A}{C_B}\right)\text{solid}}{\left(\frac{C_A}{C_B}\right)\text{liquid}}$$

wherein $C_A/C_B$ is the molar ratio of component A to component B; component A is the trans-terpenoid of formula (II-1) or (II-2); and component B represents the other components.

The inclusion ratio, $\gamma_{tr/MC}$, is a value calculated on the basis of the following equation.

$$\gamma_{tr/MC} = \frac{\text{Moles of the terpenoid in the inclusion compound}}{\text{Moles of MC in the inclusion compound}}$$

The infrared absorption spectrum of MC was as follows:
3050–2850, 1610, 1590, 1490, 1455, 1080, 890, 790, 700, 460 cm$^{-1}$.

The gas-chromatographic analysis of terpenoids was performed by a constant temperature method or a temperature raising method in the range of 100°–200° C. using "OV-17 0.5%" (a product obtained by coating 0.5% by weight of a 17:100 (weight ratio) mixture of phenyl silicone and methyl silicone on glass beads; a product of GasChro Kogyo K. K.) as a filler, and a helium gas as a carrier.

EXAMPLE 1

A sealed tube was charged with 0.1 part of MC and 0.5 part of geranyl acetone (trans content 65%), and after purging it well into nitrogen, it was heated at 130° C. for 30 minutes. The product was gradually cooled to 10° C. to precipitate crystals. The crystals were collected by filtration at room temperature, washed with a small amount of methanol, and dried at 40° C. and 0.3 mmHg for 30 minutes.

The infrared absorption spectral data and other related data of the resulting white crystals (inclusion complex compound) are shown below.
(1) MC: as given above
(2) trans-Geranylacetone (characteristic absorption): 1715, 1640 cm$^{-1}$.
(3) Inclusion complex compound:
   3050–2850, 1610, 1590, 1490, 1455, 1080, 890, 790, 700, 460, 1715, 1640 cm$^{-1}$.

It is seen from the above data that the infrared absorption spectrum of the inclusion complex compound contains absorptions of MC and the trans-geranylacetone.

Gas-chromatographic analysis showed that the proportion of the trans-geranylacetone in the geranylacetone included in the inclusion complex compound was 99%, indicating the selective inclusion of the trans-isomer. The inclusion complex compound had a selectivity of 30 and an inclusion ratio of 0.28.

Differential thermal analysis of the inclusion complex compound showed that geranyl acetone began to liberate at 130° C.

EXAMPLE 2

A sealed tube was charged with 0.15 part of MC and 0.75 part of farnesyl acetone (the trans-isomer content 36%), and after purging it well with nitrogen, it was heated at 130° C. for 30 minutes. The product was gradually cooled to about 10° C. to precipitate crystals. The crystals were collected by filtration at room temperature, washed with a small amount of methanol, and dried at 40° C. and 0.3 mmHg for 30 minutes. The infrared absorption spectral data and other related data of the resulting white crystals (inclusion complex compound) are shown below.

(1) MC: as given above
(2) trans-Farnesylacetone (characteristic absorption): 1714, 1630 cm$^{-1}$
(3) Inclusion complex compound:
3050–2850, 1610, 1590, 1490, 1455, 1080, 890, 790, 700, 460, 1714, 1630 cm$^{-1}$ It is seen from the above data that the infrared absorption spectrum of the inclusion complex compound contained absorptions of MC and the trans-farnesylacetone.

Gas-chromatographic analysis of the inclusion complex compound showed that the proportion of trans-farnesyl acetone in the farnesyl acetone included in it was 94%, indicating the selective inclusion of the trans-isomer. The inclusion complex compound had a selectivity of 24, and an inclusion ratio of 0.26.

EXAMPLE 3

A sealed tube was charged with 0.1 part of MC and 0.5 part of citral (trans-isomer content 55%), and after purging it well with nitrogen, it was heated at 130° C. for 30 minutes. The product was gradually cooled to about 10° C. to precipitate crystals. The crystals precipitated were collected by filtration at room temperature, washed with a small amount of methanol, and dried at 40° C. and 0.3 mmHg for 30 minutes. The infrared absorption spectral data and other related data of the resulting white crystals (inclusion complex compound) are shown below.

(1) MC: as given above
(2) trans-Citral (characteristic absorption): 1672, 1640, 1190 cm$^{-1}$
(3) Inclusion complex compound:
3050–2850, 1610, 1590, 1490, 1455, 1080, 890, 790, 700, 460, 1672, 1640, 1190 cm$^{-1}$ It is seen from the above data that the infrared absorption spectrum of the inclusion complex compound contained absorptions of MC and the trans-citral.

Gas-chromatographic analysis of the inclusion complex compound showed that the proportion of trans-citral in the citral included in the compound was 87%, indicating the selective inclusion of the trans-isomer. The inclusion compound had a selectivity of 5.3 and an inclusion ratio of 0.26.

EXAMPLE 4

A sealed tube was charged with 0.1 part of MC and 0.5 part of farnesal (the trans-isomer content 26%), and after purging it well with nitrogen, it was heated at 130° C. for 30 minutes. The product was gradually cooled to about 10° C. to precipitate crystals. The crystals were collected by filtration at room temperature, washed with a small amount of methanol, and dried at 40° C. and 0.3 mmHg for 30 minutes. The infrared absorption spectral data and other related data of the white crystals (inclusion complex compound) are shown below.

(1) MC: as given above
(2) trans-Farnesal (characteristic absorption): 1673, 1632, 1190, 1110 cm$^{-1}$
(3) Inclusion complex compound:
3050–2850, 1610, 1590, 1455, 1080, 890, 790, 700, 450, 1673, 1632, 1190, 1110 cm$^{-1}$ It is seen from the above data that the infrared absorption spectrum of the inclusion complex compound contained absorptions of MC and the trans-farnesal.

Gas-chromatographic analysis of the inclusion complex compound showed that the proportion of the trans-farnesal in the farnesal included in it was 98%, indicating the selective inclusion of the trans-isomer. The inclusion complex compound had a selectivity of 110 and an inclusion ratio of 0.28.

EXAMPLE 5

A sealed tube was charged with 0.1 part of MC and 0.5 part of a mixture of geraniol and nerol (geraniol content 46%), and after purging it well with nitrogen, it was heated at 130° C. for 30 minutes. The product was gradually cooled to about 10° C., and maintained at less than 15° C. to precipitate crystals. The crystals were collected by filtration at room temperature, washed with a small amount of methanol, and dried at 40° C. and 0.3 mmHg for 30 minutes. The infrared absorption spectral data and other related data of the white crystals (inclusion complex compound) are shown below.

(1) MC: as given above
(2) Geraniol (characteristic abrorption):
3450, 3050–2850, 1665, 1433, 1000 cm$^{-1}$
(3) Inclusion complex compound:
3450, 3050–2850, 1665, 1610, 1590, 1490, 1455, 1080, 1000, 890, 790, 700, 460 cm$^{-1}$ It is seen from the above data that the infrared absorption spectrum of the inclusion complex compound contained absorptions of MC and geraniol.

Gas-chromatographic analysis of the inclusion complex compound showed that the proportion of geraniol in the geraniol mixture included in it was 90%, indicating the selective inclusion of the trans-isomer. The inclusion complex compound had a selectivity of 8.7 and an inclusion ratio of 0.3.

EXAMPLE 6

A sealed tube was charged with 0.1 part of MC and 0.4 part of a mixture of geraniol and citronellol (geraniol content 46%), and after purging the tube well with nitrogen, it was heated at 130° C. for 30 minutes. The product was cooled gradually to 10° C., and maintained at less than 15° C. to precipitate crystals. The crystals were collected by filtration at room temperature, washed with a small amount of methanol, and dried at 40° C. and 0.3 mmHg for 30 minutes.

Gas-chromatographic analysis of the resulting white crystals (inclusion complex compound) showed that the proportion of geraniol in the geraniol mixture included in it was 61%, indicating the selective inclusion of the trans-isomer. The inclusion complex compound had a selectivity of 1.8 and an inclusion ratio of 0.35.

When the inclusion complex compound was subjected to differential thermal analysis, a weight decrease showing the liberation of geraniol and citronellol was observed when the temperature reached 120° C.

EXAMPLE 7

A sealed tube was charged with 0.15 part of MC and 0.5 part of a mixture of geranyl acetate and neryl acetate (geranyl acetate content 50%), and after purging the tube well with nitrogen, it was heated at 130° C. for 30 minutes. The product was cooled gradually, and maintained at less than 15° C. The crystals were collected by filtration at room temperature, washed with a small amount of methanol, and dried at 40° C. and 0.3 mmHg for 30 minutes. The infrared absorption spectral data and related data of the resulting white crystals (inclusion complex compound) are shown below:
(1) MC: as given above
(2) Geranyl acetate (characteristic absorption): 1743, 1231 cm$^{-1}$.
(3) Inclusion complex compound:
 3050–2850, 1610, 1590, 1490, 1455, 1080, 890, 790, 700, 460, 1743, 1231 cm$^{-1}$.

It is seen from the above data that the infrared absorption spectrum of the inclusion complex compound contained absorptions of MC and geranyl acetate.

Gas-chromatographic analysis of the inclusion complex compound showed that the proportion of geranyl acetate in the geranyl acetate and neryl acetate included in it was 99%, indicating the selective inclusion of the trans-isomer. The inclusion complex compound had an inclusion ratio of 0.28.

EXAMPLE 8

A sealed tube was charged with 0.05 part of MC and 0.5 part of farnesol (trans-isomer content 35%), and after purging it well with nitrogen, it was heated at 130° C. for 30 minutes. The product was cooled gradually to about 10° C., and allowed to stand at less than 15° C. to precipitate crystals. The crystals were collected by filtration at room temperature, washed with a small amount of methanol, and dried at 40° C. and 0.3 mmHg for 30 minutes. The infrared absorption spectral data and other related data of the resulting white crystals (inclusion complex compound) are shown below.
(1) MC: as given above
(2) trans-Farnesol (characteristic absorption): 3480, 1675, 1000 cm$^{-1}$.
(3) Inclusion complex compound:
 3050–2850, 1610, 1590, 1490, 1455, 1080, 890, 790, 700, 460, 3480, 1675, 1000 cm$^{-1}$.

It is seen from the above data that the infrared absorption spectrum of the inclusion complex compound contained absorptions of MC and trans-farnesol.

Gas-chromatographic analysis of the inclusion complex compound showed that the proportion of the trans-farnesol in the farnesol included in it was 87%, indicating the selective inclusion of the trans-isomer. The inclusion complex compound has a selectivity of 12 and an inclusion ratio of 0.12.

EXAMPLE 9

A sealed tube was charged with 0.1 part of MC and 0.5 part of geranic acid (trans-isomer content 55%), and after purging it well with nitrogen, it was heated at 130° C. for 30 minutes. The product was gradually cooled to about 10° C. to precipitate crystals. The crystals were separated by filtration at room temperature, washed with a small amount of methanol, and dried at 40° C. and 0.3 mmHg for 30 minutes. The infrared absorption spectral data and other related data of the resulting white crystals (inclusion complex compound) are shown below.
(1) MC: as given above
(2) trans-Geranic acid (characteristic absorption): 1690, 1633, 1247, 1170 cm$^{-1}$.
(3) Inclusion complex compound:
 3050–2850, 1610, 1590, 1490, 1455, 1080, 890, 790, 700, 460, 1690, 1633, 1247, 1170 cm$^{-1}$ It is seen from the above data that the infrared absorption spectrum of the inclusion complex compound contained absorptions of MC and trans-geranic acid.

Gas-chromatographic analysis of the inclusion complex compound showed that the proportion of the trans-geranic acid in the geranic acid included in it was 93%, indicating the selective inclusion of the trans-isomer. The inclusion complex compound had a selectivity of 10.7 and an inclusion ratio of 0.37.

EXAMPLE 10

A sealed tube was charged with 0.1 part of MC and 0.5 part of farnesic acid (trans-isomer content 35%), and after purging it well with nitrogen, it was heated at 130° C. for 30 minutes. The product was cooled gradually to about 10° C. to precipitate crystals. The crystals were collected by filtration at room temperature, washed with a small amount of methanol, and dried at 40° C. and 0.3 mmHg for 30 minutes.

Gas-chromatographic analysis of the white crystals (inclusion complex compound) showed that the proportion of the trans-farnesic acid in the farnesic acid included in it was 69%, indicating the selective inclusion of the trans-isomer. The inclusion complex compound had a selectivity of 4.1 and an inclusion ratio of 0.26.

EXAMPLE 11

A sealed tube was charged with 0.1 part of MC and 0.5 part of methyl geranate (trans-isomer content 55%), and the mixture was treated in the same way as in Example 1. The infrared absorption spectral data and other related data of the resulting white crystals (inclusion complex compound) are shown below.
(1) MC: as given above
(2) trans-Methyl geranate (characteristic absorption): 1723, 1694, 1640, 1223, 1145 cm$^{-1}$.
(3) Inclusion complex compound:
 3050–2850, 1610, 1590, 1490, 1455, 1080, 890, 790, 700, 460, 1723, 1694, 1640, 1223, 1145 cm$^{-1}$.

It is seen from the above data that the infrared absorption spectrum of the inclusion complex contained absorptions of MC and trans-methyl geranate.

Gas-chromatographic analysis of the inclusion complex compound showed that the proportion of the trans-methyl geranate in the methyl geranate included in it was 99%, indicating the selective inclusion of the trans-isomer. The inclusion complex compound had a selectivity of more than 81, and an inclusion ratio of 0.25.

EXAMPLE 12

A sealed tube was charged with 0.1 part of MC and 0.5 part of methyl farnesate (trans-isomer content 35%), and the mixture was treated in the same way as in Example 1. The infrared absorption spectrum data and other related data of the white crystals (inclusion complex compound) are shown below.
(1) MC: as given above
(2) trans-Methyl farnesate (characteristic absorption): 1720, 1640, 1220, 1142 cm$^{-1}$.
(3) Inclusion complex compound:
 3050–2850, 1610, 1590, 1490, 1455, 1080, 890, 790, 700, 460 cm$^{-1}$.

It is seen from the above data that the infrared absorption spectrum of the inclusion complex compound contained absorptions of MC and the trans-methyl farnesate.

Gas-chromatographic analysis of the inclusion complex compound showed that the proportion of the trans-methyl farnesate in the methyl farnesate included in it was 96%, indicating the selective inclusion of the transisomer. The inclusion complex compound had a selectivity of 57, and an inclusion ratio of 0.26.

EXAMPLE 13

A sealed tube was charged with 0.1 part of MC and 0.5 part of linalool, and after purging it well with nitrogen, it was heated at 130° C. for 30 minutes. The product was gradually cooled to about 10° C. to precipitate crystals. The crystals were collected by filtration at room temperature, washed with a small amount of methanol, and dried at 40° C. and 0.3 mmHg for 30 minutes. The infrared absorption spectral data and other related data of the resulting white crystals (inclusion complex compound) are shown below.

(1) MC: as given above
(2) Linalool (characteristic absorption):
    3400, 1640, 995, 920 cm$^{-1}$.
(3) Inclusion complex compound:
    3050–2850, 1610, 1590, 1490, 1455, 1080, 890, 790, 700, 460, 3400, 1640, 995, 920 cm$^{-1}$.

It is seen from the above data that the infrared absorption spectrum of the inclusion complex compound contained absorptions of MC and linalool.

Gas-chromatographic analysis of the inclusion complex compound showed that the ratio of linalool included in it was 0.46.

EXAMPLE 14

A sealed tube was charged with 0.2 part of MC and 0.5 part of a mixture of linalool and nerol (linalool content 66%), and after purging it well with nitrogen, it was heated at 130° C. for 30 minutes. The product was cooled gradually to about 10° C. to precipitate crystals. The crystals were collected by filtration at room temperature, washed with a small amount of methanol, and dried at 40° C. and 0.3 mmHg for 30 minutes.

Gas-chromatographic analysis of the resulting white crystals (inclusion complex compound) showed that the proportion of linalool in the linalool nerol mixture included in it was 99%, indicating the selective inclusion of the trans-isomer. The inclusion complex had a selectivity of 51 and an inclusion ratio of 0.42.

EXAMPLE 15

A sealed tube was charged with 0.5 part of MC and 0.5 part of nerolidol (trans-isomer content 60%), and the mixture was treated in the same way as in Example 1. The infrared absorption spectral data and other related data of the resulting white crystals (inclusion complex compound) are shown below.

(1) MC: as given above
(2) trans-Nerolidol (characteristic absorption): 3440, 1640 cm$^{-1}$.
(3) Inclusion complex compound: 3050–2850, 1610, 1590, 1490, 1455, 1080, 890, 790, 700, 460, 3440, 1640 cm$^{-1}$.

It is seen from the above data that the infrared absorption spectrum of the inclusion complex compound contained absorptions of MC and the trans-nerolidol.

Gas-chromatographic analysis of the inclusion complex compound showed that the proportion of the trans-nerolidol in the nerolidol included in it was 97%, indicating the selective inclusion of the trans-isomer. The inclusion complex compound had an inclusion ratio of 0.35.

EXAMPLE 16

A sealed tube was charged with 0.25 part of MC and 0.5 part of geranyl linalool (trans-isomer content 35%), and the mixture was treated in the same way as in Example 1. The infrared absorption spectral data and other related data of the resulting white crystals (inclusion complex compound) are shown below.

(1) MC: as given above
(2) trans-Geranyl linalool (characteristic absorption): 3440, 1640, 1000 cm$^{-1}$.
(3) Inclusion complex compound:
    3050–2850, 1610, 1590, 1490, 1455, 1080, 890, 790, 700, 460, 3440, 1640, 1000 cm$^{-1}$.

It is seen from the above data that the infrared absorption spectrum of the inclusion complex compound contained absorptions of MC and the trans-geranyl linalool.

Gas-chromatographic analysis of the inclusion complex compound showed that the proportion of the trans-geranyl linalool in the geranyl linalool included in it was 81%, indicating the selective inclusion of the trans-isomer. The inclusion complex compound had a selectivity of 8.2, and an inclusion ratio of 0.32.

EXAMPLE 17

A mixture of 0.1 part of MC, and 0.2 part of 2,7,11,15,19-pentamethyl-3-hydroxyeicosa-1,6,10,14,18-pentaene (trans-isomer content 69%) was heated at 120° C. for 5 minutes to form a uniform mixture. The mixture was allowed to cool to precipitate crystals. The crystals were collected by filtration at room temperature, well washed with 25 parts of isopropanol, and dried overnight at 20 mmHg. The infrared absorption spectral data of the resulting inclusion compound were as follows:

3050–2850, 1610, 1590, 1490, 1455, 1080, 890, 790, 700 cm$^{-1}$.

Gas-chromatographic analysis and $C_{13}$ NMR spectroscopy showed that the compound included in the crystals was only the trans-isomer.

EXAMPLE 18

A mixture of 0.1 part of MC and 0.2 part of 3,7,11,15,19,23-hexamethyl-3-hydroxypentacosa-1,6,10,14,18,22-hexaene (trans-isomer content about 50%) was heated at 120° C. for 5 minutes to form a uniform mixture. The mixture was allowed to cool to precipitate crystals. The crystals were collected by filtration at room temperature, washed well with 25 parts of isopropanol, and then dried overnight at 20 mmHg. The infrared absorption spectral data of the resulting crystals (inclusion complex compound) were as follows:

3050–2850, 1610, 1590, 1490, 1455, 1080, 890, 790, 700 cm$^{-1}$.

Gas-chromatographic analysis showed that the compound included in the crystals was only the trans-isomer.

What we claim is:

1. An inclusion complex compound comprising (a) meta-cyclophane of the formula

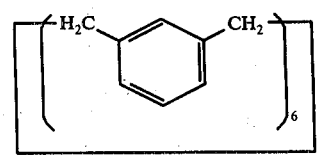

and (b) a trans-terpenoid of the formula

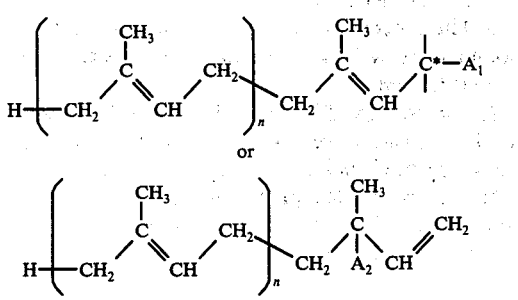

wherein n is an integer of 1 to 9; $A_1$ and $A_2$ each represent (1) a hydrogen atom, (2) a halogen atom, (3) an inorganic group containing an oxygen, nitrogen or sulfur atom, (4) an organic group containing 1 to 5 carbon atoms, or (5) an organic group containing an oxygen, nitrogen or sulfur atom and 1 to 5 carbon atoms; and C* is the carbon atom of a carbonyl or methylene group, included by the meta-cyclophane.

2. An inclusion complex compound comprising (a) meta-cyclophane of the formula

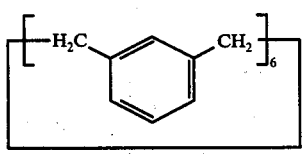

and (b) a trans-terpenoid of the formula

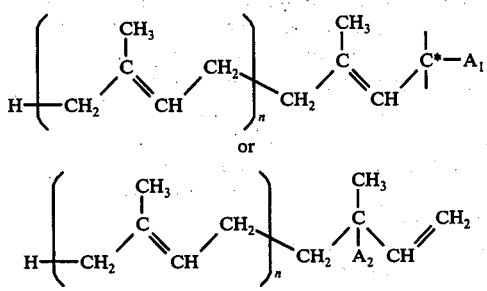

wherein n is an integer of 1 to 5; $A_1$ and $A_2$ each represent (1) a hydrogen atom, (2) a halogen atom selected from chlorine, bromine and iodine, (3) an inorganic group selected from the group consisting of —OH, —NH$_2$, —NO$_2$, —SH, —SCN and —SO$_3$H, (4) an alkyl group containing 1 to 5 carbon atoms, or (5) a group selected from the group consisting of —OR, $$-\underset{\underset{O}{\|}}{C}-R, \quad -O-\underset{\underset{O}{\|}}{C}-R,$$

—NHR, —N=N—R, —SO$_2$R and —SR in which R is an alkyl group containing 1 to 5 carbon atoms; C* is the carbon atom of a carbonyl or methylene group, included by the meta-cyclophane.

3. An inclusion complex compound comprising (a) meta-cyclophane of the formula

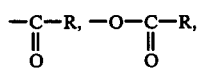

and (b) a trans-terpenoid of the formula

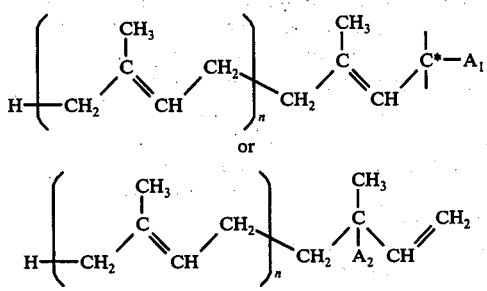

wherein n is an integer of 1 to 5; $A_1$ and $A_2$ each represent —H, —Cl, —Br, —OH, —NH$_2$, —NO$_2$, —SH, —SO$_3$H, —CH$_3$, —OR, $$-\underset{\underset{O}{\|}}{C}-R, \quad -O-\underset{\underset{O}{\|}}{C}-R,$$

—NHR, or —SR in which R is an alkyl group containing 1 to 5 carbon atoms; these atoms or groups may be bonded to a carbon atom through an alkylene group, in which case the number of carbon atoms of the alkylene group and that of carbon atoms of the group R is not more than 5; and C* is the carbon atom of a carbonyl or methylene group, included by the meta-cyclophane.

4. A process for producing an inclusion complex compound comprising meta-cyclophane of the formula

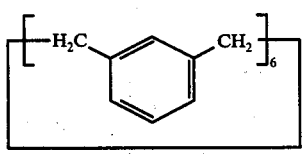

and (b) a trans-terpenoid of the formula

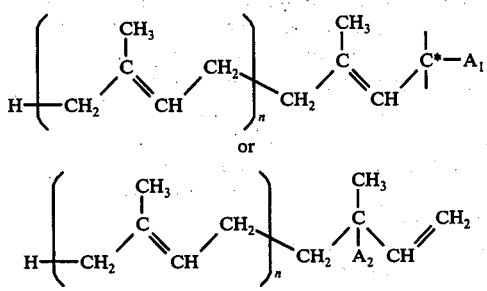

wherein n is an integer of 1 to 9; $A_1$ and $A_2$ each represent (1) a hydrogen atom, (2) a halogen atom, (3) an inorganic group containing an oxygen, nitrogen or sulfur atom, (4) an organic group containing 1 to 5 carbon atoms, or (5) an organic group containing an oxygen, nitrogen or sulfur atom and 1 to 5 carbon atoms; and C* is the carbon atom of a carbony, or methylene group, included by the meta-cyclophane, which comprises contacting the meta-cyclophane with a mixture containing the trans-terpenoid.

5. The process of claim 4 wherein the amount of the meta-cyclophane is 0.01 to 100 moles per mole of the trans-terpenoid contained in the mixture.

6. The process of claim 5 wherein the contacting is performed at a temperature of −50° C. to 350° C.

7. A process for separating a trans-terpenoid from a mixture containing it, which comprises contacting meta-cyclophane of the formula

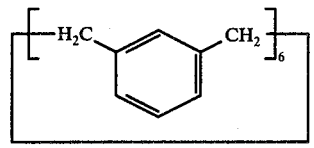

with a trans-terpenoid of the formula

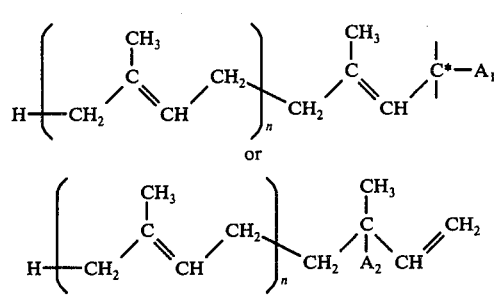

wherein n is an integer of 1 to 9; $A_1$ and $A_2$ each represent (1) a hydrogen atom, (2) a halogen atom, (3) an inorganic group containing an oxygen, nitrogen or sulfur atom, (4) an organic group containing 1 to 5 carbon atoms, or (5) an organic group containing an oxygen, nitrogen or sulfur atom and 1 to 5 carbon atoms; and C* is the carbon atom of a carbonyl or methylene group, to form an inclusion complex compound comprising the meta-cyclophane and the trans-terpenoid included by it, separating the inclusion complex compound from the mixture, and then separating the included trans-terpenoid from the inclusion complex compound.

8. The process of claim 7 wherein the inclusion compound is heated to evaporate the trans-terpenoid included therein.

9. The process of claim 7 wherein a solvent is applied to the inclusion complex compound to separate the trans-terpenoid included therein.

10. A process for producing an inclusion complex compound which comprises contacting metacyclophane of the formula:

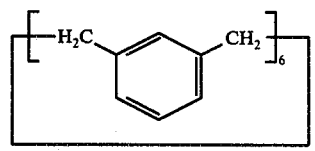

with a mixture containing a trans-terpenoid of the formula:

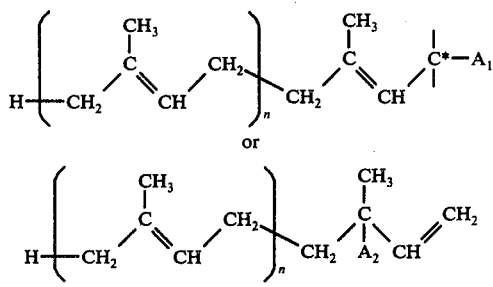

wherein n is an integer of 1 to 9; $A_1$ and $A_2$ each represent (1) a hydrogen atom, (2) a halogen atom, (3) an inorganic group containing an oxygen, nitrogen or sulfur atom, (4) an organic group containing 1 to 5 carbon atoms; and C* is the carbon atom of a carbonyl or methylene group, to form an inclusion complex compound comprising the metacyclophane and the trans-terpenoid included by it, and then separating the inclusion complex compound from the mixture.

11. An inclusion complex compound produced by the process of claim 4.

* * * * *